US008497304B2

(12) United States Patent
Sawa et al.

(10) Patent No.: US 8,497,304 B2
(45) Date of Patent: Jul. 30, 2013

(54) AQUEOUS LIQUID PREPARATION CONTAINING 2-AMINO-3-(4-BROMOBENZOYL)PHENYLACETIC ACID

(75) Inventors: Shirou Sawa, Kobe (JP); Shuhei Fujita, Kakogawa (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/353,653

(22) Filed: Jan. 19, 2012

(65) Prior Publication Data
US 2012/0115957 A1  May 10, 2012

Related U.S. Application Data

(62) Division of application No. 10/525,006, filed as application No. PCT/JP2004/000350 on Jan. 16, 2004, now Pat. No. 8,129,431.

(30) Foreign Application Priority Data

Jan. 21, 2003 (JP) ................................ 2003-012427

(51) Int. Cl.
| A01N 37/18 | (2006.01) |
| A01N 37/44 | (2006.01) |
| A01N 37/10 | (2006.01) |
| A61K 31/165 | (2006.01) |
| A61K 31/24 | (2006.01) |
| A61K 31/19 | (2006.01) |

(52) U.S. Cl.
USPC ............ 514/619; 514/535; 514/570; 514/618

(58) Field of Classification Search
USPC .......................................... 514/619, 535, 570
See application file for complete search history.

(56) References Cited

U.S. PATENT DOCUMENTS

| 4,045,576 | A |   | 8/1977  | Welstead, Jr. et al. |
| 4,683,242 | A |   | 7/1987  | Poser |
| 4,910,225 | A |   | 3/1990  | Ogawa et al. |
| 5,110,493 | A |   | 5/1992  | Cherng-Chyi et al. |
| 5,475,034 | A |   | 12/1995 | Yanni et al. |
| 5,540,930 | A |   | 7/1996  | Guy |
| 5,597,560 | A |   | 1/1997  | Bergamini et al. |
| 5,603,929 | A |   | 2/1997  | Desai et al. |
| 5,653,972 | A |   | 8/1997  | Desai et al. |
| 5,942,508 | A | * | 8/1999  | Sawa ........................ 514/235.8 |
| 5,998,465 | A |   | 12/1999 | Hellberg et al. |
| 6,274,592 | B1 | * | 8/2001  | Sawa ............................ 514/291 |
| 6,319,513 | B1 |   | 11/2001 | Dobrozsi |
| 6,369,112 | B1 |   | 4/2002  | Xia |
| 6,383,471 | B1 | * | 5/2002  | Chen et al. ...................... 424/45 |
| 6,395,746 | B1 |   | 5/2002  | Cagle et al. |
| 2001/0056098 | A1 | * | 12/2001 | Sawa ............................ 514/258 |
| 2007/0082857 | A1 |   | 4/2007  | Sawa |

FOREIGN PATENT DOCUMENTS

| AU | 707 119      |   | 9/1995  |
| CA | 2 013 188    |   | 9/1990  |
| JP | 02083323 A   | * | 3/1990  |
| JP | 5-223052     |   | 8/1993  |
| JP | 11-228404    |   | 8/1999  |
| JP | 2002308764 A | * | 10/2002 |
| WO | 96/14829     |   | 5/1996  |
| WO | 01/15677     |   | 3/2001  |
| WO | WO 0115677 A2 | * | 3/2001  |
| WO | 02/13804     |   | 2/2002  |

OTHER PUBLICATIONS

New Drugs in Japan, 2001, 2001 Edition, Published by Yakuji Nippo Ltd., May 11, 2001, pp. 27-29, and its English translation of the material portions.
ISTA Pharmaceuticals, "New Drug Applications: Xibrom", http://www.drugs.com/nda/xibrom_040525.htmt, accessed online Sep. 19, 2007.
Nolan et al., "The Topical Anti-Inflammatory and Analgesic Properties of Bromfenic in Rodents", Agents and Actions, vol. 25, No. 1-2, pp. 77-85, Aug. 1988.
Corrected partial English translation of New Drugs in Japan, 2001, 2001 Edition, Published by Yakuji Nippo Ltd., May 11, 2001, pp. 27-29, previously submitted on Apr. 11, 2005.
Complete English translation of New Drugs in Japan, 2001, 2001 Edition, Published by Yakuji Nippo Ltd., May 11, 2001, pp. 27-29.
Notice of Opposition dated Feb. 19, 2009 issued by EPO in connection with the corresponding European patent application and Opposition.
http://medical-dictionary.thefreedictionary.com/prophylactic accessed Dec. 15, 2009.

* cited by examiner

*Primary Examiner* — Layla Soroush
(74) *Attorney, Agent, or Firm* — Wenderoth, Lind & Ponack, LLP.

(57) ABSTRACT

An aqueous liquid preparation of the present invention containing 2-amino-3-(4-bromobenzoyl)phenylacetic acid or its pharmacologically acceptable salt or a hydrate thereof, an alkyl aryl polyether alcohol type polymer such as tyloxapol, or a polyethylene glycol fatty acid ester such as polyethylene glycol monostearate is stable. Since even in the case where a preservative is incorporated into said aqueous liquid preparation, the preservative exhibits a sufficient preservative effect for a long time, said aqueous liquid preparation in the form of an eye drop is useful for the treatment of blepharitis, conjunctivitis, scleritis, and postoperative inflammation. Also, the aqueous liquid preparation of the present invention in the form of a nasal drop is useful for the treatment of allergic rhinitis and inflammatory rhinitis (e.g. chronic rhinitis, hypertrophic rhinitis, nasal polyp, etc.).

17 Claims, No Drawings

AQUEOUS LIQUID PREPARATION CONTAINING 2-AMINO-3-(4-BROMOBENZOYL)PHENYLACETIC ACID

This is a divisional of Ser. No. 10/525,006, filed Mar. 28, 2005 now U.S. Pat. No. 8,129,431, which is a U.S. national stage of International Application No. PCT/JP2004/000350 filed Jan. 16, 2004.

TECHNICAL FIELD

The present invention relates to an aqueous liquid preparation containing 2-amino-3-(4-bromobenzoyl)phenylacetic acid or a pharmacologically acceptable salt thereof or a hydrate thereof. More particularly, the present invention relates to an aqueous liquid preparation containing 2-amino-3-(4-bromobenzoyl)phenylacetic acid or a pharmacologically acceptable salt thereof or a hydrate thereof and an alkyl aryl polyether alcohol type polymer or a polyethylene glycol fatty acid ester.

BACKGROUND ART

Benzoylphenylacetic acid derivatives including bromfenac (generic name) of formula (I):

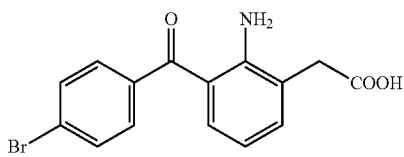 [SMILES: Nc1c(CC(=O)O)cccc1C(=O)c1ccc(Br)cc1]

of which chemical name is 2-amino-3-(4-bromobenzoyl) phenylacetic acid are known as disclosed in JP-A-23052/1977 and its corresponding U.S. Pat. No. 4,045,576. 2-Amino-3-(4-bromobenzoyl)phenylacetic acid, its pharmacologically acceptable salt and a hydrate thereof are known as a non-steroidal anti-inflammatory agent, and they are effective against inflammatory diseases of anterior or posterior segment of the eye, such as blepharitis, conjunctivitis, scleritis, and postoperative inflammation in the field of ophthalmology, and its sodium salt has been practically used in the form of eye drops ("New Drugs in Japan, 2001", 2001 Edition, Published by Yakuji Nippo Ltd., May 11, 2001, p. 27-29).

The eye drop as mentioned above is designed to stabilize 2-amino-3-(4-bromobenzoyl)phenylacetic acid by means of addition of a water-soluble polymer (e.g. polyvinylpyrrolidone, polyvinyl alcohol, etc.) and a sulfite (e.g. sodium sulfite, potassium sulfite, etc.) (Japanese patent No. 2,683,676 and its corresponding U.S. Pat. No. 4,910,225).

In addition, as an eye drop other than the above-mentioned one, Japanese patent No. 2,954,356 (corresponding to U.S. Pat. Nos. 5,603,929 and 5,653,972) discloses a stable ophthalmic composition which comprises incorporating an antibacterial quaternary ammonium polymer and boric acid into an acidic ophthalmic agent. The acidic agent described therein includes, for example, 2-amino-3-(4-bromobenzoyl) phenylacetic acid.

Further, in Japanese patent No. 2,954,356, there is the following description—"Benzalkonium chloride is a widely used preservative in ophthalmic solutions. However, benzalkonium chloride and other quaternary ammonium compounds are generally considered to be incompatible with ophthalmic compositions of drugs with acidic groups, such as nonsteroidal anti-inflammatory drugs. These preservatives lose their ability to function as they form complexes with the charged drug compounds".

In these prior art references, there is no disclosure that alkyl aryl polyether alcohol type polymers or polyethylene glycol fatty acid esters are able to stabilize an aqueous liquid preparation of 2-amino-3-(4-bromobenzoyl)phenylacetic acid or its pharmacologically acceptable salt, and inhibit decrease in preservative effect of benzalkonium chloride and other quaternary ammonium compounds.

DISCLOSURE OF THE INVENTION

It is an object of the present invention to provide an aqueous liquid preparation comprising 2-amino-3-(4-bromobenzoyl)phenylacetic acid or a pharmacologically acceptable salt thereof or a hydrate thereof, which is stable within a pH range giving no irritation to eyes and in which, when a preservative such as benzalkonium chloride is incorporated therein, preservative effect of the preservative does not substantially deteriorate.

Another object of the invention is to provide a method for stabilizing an aqueous liquid preparation of 2-amino-3-(4-bromobenzoyl)phenylacetic acid or a pharmacologically acceptable salt thereof or a hydrate thereof.

Further object of the invention is to provide an aqueous liquid preparation comprising 2-amino-3-(4-bromobenzoyl) phenylacetic acid or a pharmacologically acceptable salt thereof or a hydrate thereof and a preservative, wherein, when specifically a quaternary ammonium salt such as benzalkonium chloride is incorporated as a preservative, decrease in preservative effect of said preservative is inhibited.

As a result of various studies, the inventors of the present invention have found that, by adding, for example, an alkyl aryl polyether alcohol type polymer such as tyloxapol, or a polyethylene glycol fatty acid ester such as polyethylene glycol monostearate to an aqueous liquid preparation of 2-amino-3-(4-bromobenzoyl)phenylacetic acid or a pharmacologically acceptable salt thereof or a hydrate thereof, the aqueous solution becomes stable within a pH range giving no irritation to eyes, and change of the 2-amino-3-(4-bromobenzoyl)phenylacetic acid over time can be inhibited, and furthermore, when the aqueous solution contains a preservative, deterioration in the preservative effect of said preservative can be inhibited for a long period of time. The inventors of the present invention have further studied extensively and completed the present invention.

Namely, the present invention relates to:
(1) An aqueous liquid preparation comprising 2-amino-3-(4-bromobenzoyl)phenylacetic acid or a pharmacologically acceptable salt thereof or a hydrate thereof, and an alkyl aryl polyether alcohol type polymer or a polyethylene glycol fatty acid ester,
(2) The aqueous liquid preparation according to the above (1), wherein the alkyl aryl polyether alcohol type polymer has a polymerization degree of 3 to 10, the alkyl contains 1 to 18 carbon atoms, the aryl is a phenyl residue, and the polyether alcohol is represented by the formula $O(CH_2CH_2O)_xH$ in which X is an integer of 5 to 100,
(3) The aqueous liquid preparation according to the above (1) or (2), wherein the alkyl aryl polyether alcohol type polymer is tyloxapol,
(4) The aqueous liquid preparation according to the above (1), wherein the carbon number of the fatty acid in the polyethylene glycol fatty acid ester is 12 to 18, (5) The aqueous liquid preparation according to the above (1) or (4), wherein the polyethylene glycol fatty acid ester is polyethylene glycol monostearate, (6) The aqueous liquid preparation according to any one of the above (1) to (3), wherein the concentration of the alkyl aryl polyether alcohol type polymer is selected from a range of minimum concentration of 0.01 w/v % to maximum concentration of 0.5 w/v %, (7) The aqueous liquid preparation according to any one of the above (1), (2) or (4), wherein the concentration of the polyethylene glycol fatty acid ester is selected from a range of minimum concentration of 0.02 w/v % to maximum concentration of 0.1 w/v %, (8) The aqueous liquid preparation according to any one of the above (1) to (7), wherein the concentration of the 2-amino-3-(4-bromobenzoyl)phenylacetic acid or a pharmacologically acceptable salt thereof or a hydrate thereof is 0.01 to 0.5 w/v %, (9) The aqueous liquid preparation according to any one of the above (1) to (8), wherein benzalkonium chloride is contained as a preservative,

(10) The aqueous liquid preparation according to anyone of the above (1) to (9), wherein the pharmacologically acceptable salt of 2-amino-3-(4-bromobenzoyl)phenylacetic acid is a sodium salt,

(11) The aqueous liquid preparation according to any one of the above (1) to (10), wherein the pH of the aqueous liquid preparation is within a range of 7 to 9,

(12) The aqueous liquid preparation according to the above (11), wherein the pH of the aqueous liquid preparation is within a range of 7.5 to 8.5,

(13) The aqueous liquid preparation according to any one of the above (1) to (12), wherein the aqueous liquid preparation is an eye drop,

(14) The aqueous liquid preparation according to any one of the above (1) to (12), wherein the aqueous liquid preparation is a nasal drop,

(15) An eye drop comprising sodium 2-amino-3-(4-bromobenzoyl)phenylacetate hydrate and 0.01 to 0.5 w/v % of tyloxapol,

(16) An eye drop comprising sodium 2-amino-3-(4-bromobenzoyl)phenylacetate hydrate and 0.02 to 0.1 w/v % of polyethylene glycol monostearate,

(17) A method for stabilizing 2-amino-3-(4-bromobenzoyl)phenylacetic acid or a pharmacologically acceptable salt thereof or a hydrate thereof in an aqueous liquid preparation, which comprises incorporating tyloxapol or polyethylene glycol monostearate into an aqueous liquid preparation containing 2-amino-3-(4-bromobenzoyl)phenylacetic acid or a pharmacologically acceptable salt thereof or a hydrate thereof, and

(18) A method for inhibiting decrease in preservative effect of a preservative in an aqueous liquid preparation of 2-amino-3-(4-bromobenzoyl)phenylacetic acid or a pharmacologically acceptable salt thereof or a hydrate thereof, which comprises incorporating tyloxapol or polyethylene glycol monostearate into an aqueous liquid preparation containing 2-amino-3-(4-bromobenzoyl)phenylacetic acid or a pharmacologically acceptable salt thereof or a hydrate thereof and a preservative.

According to the present invention, a stable aqueous liquid preparation containing 2-amino-3-(4-bromobenzoyl)phenylacetic acid or a pharmacologically acceptable salt thereof or a hydrate thereof can be prepared by incorporating an alkyl aryl polyether alcohol type polymer such as tyloxapol, or a polyethylene glycol fatty acid ester such as polyethylene glycol monostearate into an aqueous liquid preparation containing 2-amino-3-(4-bromobenzoyl)phenylacetic acid or a pharmacologically acceptable salt thereof or a hydrate thereof. Also, an aqueous liquid preparation of the present invention, wherein a preservative is incorporated, has a sufficient preservative effect.

Therefore, the aqueous liquid preparation of the present invention is advantageously used as an eye drop for the treatment of, for example, blepharitis, conjunctivitis, scleritis, and postoperative inflammation. In addition, such aqueous liquid preparation can be used as a nasal drop for the treatment of, for example, allergic rhinitis and inflammatory rhinitis (e.g. chronic rhinitis, hypertrophic rhinitis, nasal polyp, etc.).

The pharmacologically acceptable salt of 2-amino-3-(4-bromobenzoyl)phenylacetic acid includes, for example, an alkali metal salt such as sodium salt and potassium salt, and an alkaline earth metal salt such as calcium salt and magnesium salt, among which sodium salt is especially preferable.

2-Amino-3-(4-bromobenzoyl)phenylacetic acid and its pharmacologically acceptable salt can be prepared according to the method as described in JP-A-23052/1977 (corresponding to U.S. Pat. No. 4,045,576) or by a similar method thereof. These compounds can be obtained as their hydrate depending on synthetic conditions and recrystallization conditions. The hydrate includes 1/2 hydrate, 1 hydrate, and 3/2 hydrate, among which 3/2 hydrate is preferable.

In the aqueous liquid preparation of the present invention, the content (concentration range) of 2-amino-3-(4-bromobenzoyl)phenylacetic acid or a pharmacologically acceptable salt thereof or a hydrate thereof is usually about 0.01 to 0.5 w/v %, preferably about 0.05 to 0.2 w/v %, especially about 0.1 w/v %, and it is preferable to appropriately vary the content depending on the purpose of use and the degree of disease to be treated.

The carbon number of the alkyl in the an alkyl aryl polyether alcohol type polymer which is a non-ionic surfactant used as a stabilizer for 2-amino-3-(4-bromobenzoyl)phenylacetic acid or a pharmacologically acceptable salt thereof or a hydrate thereof is approximately 1 to 18. Specifically, the alkyl group includes, for example, methyl, ethyl, propyl, isopropyl, cyclopropyl, butyl, isobutyl, sec-butyl, tert-butyl, cyclobutyl, pentyl, isopentyl, neopentyl, tert-pentyl, 1-ethylpropyl, 4-methylpentyl, 1,1-dimethylbutyl, 2,2-dimethylbutyl, 1,2-dimethylbutyl, 2-ethylbutyl, cyclopentyl, hexyl, cyclohexyl, heptyl, isoheptyl, octyl, isooctyl, nonyl, isononyl, decyl, isodecyl, undecyl, isoundecyl, dodecyl, isododecyl, tridecyl, isotridecyl, tetradecyl, isotetradecyl, pentadecyl, isopentadecyl, hexadecyl, isohexadecyl, heptadecyl, isoheptadecyl, octadecyl, isooctadecyl, and isomers thereof, among which octyl and its isomer (e.g. isooctyl, sec-octyl, 1-methylheptyl, 1-ethylhexyl, 2-ethylhexyl, 1-propylpentyl, 1,5-dimethylhexyl, 1,1,3,3-tetramethylbutyl, etc.) are preferable, and 1,1,3,3-tetramethylbutyl which is an isomer of octyl groups is especially preferable.

The aryl in the alkyl aryl polyether alcohol type polymer can be preferably a phenyl residue. The polyether alcohol can be represented by the formula $O(CH_2CH_2O)_xH$ in which X is an integer of 5 to 100, preferably 5 to 30, more preferably 8 to 10. The average polymerization degree is preferably about 3 to 10.

Among the above-mentioned alkyl aryl polyether alcohol type polymers, tyloxapol having the following formula is especially preferable.

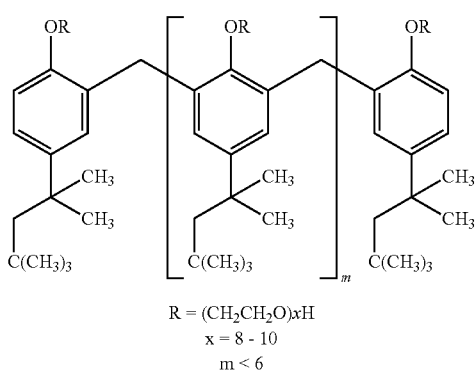

R = (CH₂CH₂O)xH
x = 8 - 10
m < 6

The fatty acid of the polyethylene glycol fatty acid ester which is a non-ionic surfactant used as a stabilizer for 2-amino-3-(4-bromobenzoyl)phenylacetic acid or a pharmacologically acceptable salt thereof or a hydrate thereof can be preferably a fatty acid having the carbon number of 12 to 18. Specific examples of such polyethylene glycol fatty acid esters are polyethylene glycol monostearate (e.g. polyoxyl 8 stearate, polyoxyl 40 stearate, etc.), polyethylene glycol monolaurate, polyethylene glycol monooleate, polyethylene glycol diisostearate, polyethylene glycol dilaurate, polyethylene glycol dioleate, and the like. Among these compounds, polyethylene glycol monostearate is preferable, and polyoxyl 40 stearate is especially preferable. The polyoxyl 40 stearate is a monostearic acid ester of an ethylene oxide condensed polymer, and can be represented by the formula $C_{17}H_{35}COO(CH_2CH_2O)_nH$ which is a non-ionic surfactant and n is about 40.

Although the content (concentration range) of the alkyl aryl polyether alcohol type polymer in the aqueous liquid preparation of the present invention depends on the kind of compounds used, the minimum concentration is about 0.01 w/v and the maximum concentration is about 0.5 w/v %. With respect to the tyloxapol content (concentration range), for example, the minimum content is about 0.01 w/v %, 0.02 w/v % or 0.03 w/v %, and the maximum content is about 0.05 w/v %, 0.1 w/v %, 0.3 w/v % or 0.5% w/v, and preferably the minimum content is about 0.02 w/v % and the maximum content is about 0.05 w/v %.

Although the content (concentration range) of the polyethylene glycol fatty acid ester in the aqueous liquid preparation of the present invention depends on the kind of compounds used, it is within a range of about 0.02 w/v % of minimum concentration to about 0.1 w/v % of maximum concentration. For example, the content (concentration range) of polyethylene glycol monostearate is within a range of about 0.02 w/v % of minimum content to about 0.1 w/v of maximum content, and preferably within a range of about 0.02 w/v % of the minimum content to about 0.05 w/v % of the maximum content.

The incorporation ratio of tyloxapol in the aqueous liquid preparation of the invention is within a range of the minimum content of about 0.1 or 0.2 part by weight to the maximum content of about 0.5, 1, 3 or 5 parts by weight, relative to 1 part by weight of 2-amino-3-(4-bromobenzoyl)phenylacetic acid or its pharmacologically acceptable salt or a hydrate thereof.

The incorporation ratio of polyethylene glycol monostearate in the aqueous liquid preparation of the present invention is within a range of the minimum content of about 0.2 part by weight to the maximum content of about 0.5 or 1 part by weight, relative to 1 part by weight of 2-amino-3-(4-bromobenzoyl)phenylacetic acid or its pharmacologically acceptable salt or a hydrate thereof.

The preservative used in the present invention includes, for example, quaternary ammonium salts (e.g. benzalkonium chloride, benzethonium chloride, etc.), chlorhexidine gluconate, and the like, among which benzalkonium chloride is especially preferable.

Further, so long as the purpose of the present invention is achieved, conventional various additives such as isotonics, buffers, thickners, stabilizers, chelating agents, pH controlling agents, perfumes and the like may be appropriately added to the aqueous liquid preparation of the present invention. The isotonics include sodium chloride, potassium chloride, glycerine, mannitol, sorbitol, boric acid, glucose, propylene glycol and the like. The buffers include, for example, phosphate buffer, borate buffer, citrate buffer, tartarate buffer, acetate buffer, boric acid, borax, amino acids, and the like. The thickners include polyvinylpyrrolidone, carboxymethylcellulose, carboxypropylcellulose, hydroxyethylcellulose, hydroxypropylcellulose, hydroxypropylmethylcellulose, polyvinyl alcohol, sodium polyacrylate, and the like. The stabilizers include sulfites such as sodium sulfite and the like. The chelating agents include sodium edetate, sodium citrate, condensed sodium phosphate and the like. The pH controlling agents include hydrochloric acid, sodium hydroxide, phosphoric acid, acetic acid and the like. The perfumes include 1-menthol, borneol, camphor, Eucalyptus oil, and the like.

With respect to the concentrations of the above various additives in the aqueous liquid preparation of the present invention, the isotonic is incorporated into an osmotic pressure ratio of about 0.8 to 1.2, and the concentrations of the buffer and the thickner to be added are about 0.01 to 2 w/v % and 0.1 to 10 w/v %, respectively.

The pH of the aqueous liquid preparation of the present invention is adjusted to about 6 to 9, preferably about 7 to 9, especially about 7.5 to 8.5.

So long as the purpose of the present invention is achieved, other same or different kind of active ingredients may be appropriately added.

The aqueous liquid preparation of the present invention can be prepared by per se known method or according to the method as described in the Japanese Pharmacopoeia 14$^{th}$ Edition, General Rules for Preparations, Solutions or Ophthalmic solutions.

The aqueous liquid preparation of the present invention can be applied to warm-blooded animals such as human, rat, mouse, rabbit, cow, pig, dog, cat, and the like.

The aqueous liquid preparation of the present invention can be prepared easily by dissolving the above-mentioned components in, for example, distilled water or sterile purified water. For example, the aqueous liquid preparation in the form of an eye drop can be used for the treatment of inflammatory diseases in anterior or posterior segment of the eye such as blepharitis, conjunctivitis, scleritis, postoperative inflammation, and the like. The dose of the aqueous liquid preparation containing 0.1 w/v % of sodium 2-amino-3-(4- bromobenzoyl)phenylacetate hydrate is, for example, administered to an adult 3 to 6 times daily in an amount of 1 to 2 drops per one time. Depending on the degree of diseases, frequency of dosing is appropriately controlled.

BEST MODE FOR CARRYING OUT THE INVENTION

The present invention is illustrated by way of the following Experimental Examples and Working Examples, but it is not restricted by these Examples.

EXPERIMENTAL EXAMPLE 1

Stability Test of Sodium 2-amino-3-(4-bromobenzoyl)phenylacetate

Four eye drops of sodium 2-amino-3-(4-bromobenzoyl)phenylacetate comprising the components as shown in Table 1 were prepared, filled respectively into a polypropylene container and subjected to stability test at 60° C.

TABLE 1

| Component | Comparison Example 1 | A-01 | A-02 | A-03 |
|---|---|---|---|---|
| Sodium 2-amino-3-(4-bromobenzoyl)phenyl-acetate | 0.1 g | 0.1 g | 0.1 g | 0.1 g |
| Boric acid | 1.5 g | 1.5 g | 1.5 g | 1.5 g |
| Benzalkonium chloride | 0.005 g | 0.005 g | 0.005 g | 0.005 g |
| Polysorbate 80 | 0.15 g | — | — | — |
| Polyoxyl 40 stearate | — | 0.15 g | — | — |
| Tyloxapol | — | — | 0.15 g | 0.02 g |
| Sterile purified water | q.s. | q.s. | q.s. | q.s |
| Total volume | 100 mL | 100 mL | 100 mL | 100 mL |
| pH | 7.0 | 7.0 | 7.0 | 7.0 |
| Remaining rate (%) at 60° C. after 4 weeks | 51.3 | 63.7 | 73.8 | 89.6 |

The remaining rate (%) in the above Table 1 indicates values obtained by correcting moisture vaporization from the container. As is apparent from the Table 1, stability test was carried out under the conditions of pH 7.0 at 60° C. for 4 weeks, and sodium 2-amino-3-(4-bromobenzoyl)phenylacetate in each eye drop was stable in the order of tyloxapol-containing preparation>polyoxyl 40 stearate-containing preparation>polysorbate 80-containing preparation.

Further, with respect to eye drops containing tyloxapol (compositions A-02 and A-03), sodium 2-amino-3-(4-bromobenzoyl)phenylacetate in composition A-03 containing 0.02 w/v % of tyloxapol is more stable than that in composition A-02 containing 0.15 w/v % of tyloxapol.

EXPERIMENTAL EXAMPLE 2

Stability Test of Sodium 2-amino-3-(4-bromobenzoyl)phenylacetate

Five eye drops of sodium 2-amino-3-(4-bromobenzoyl) phenylacetate comprising the components as shown in Table 2 were prepared, filled respectively into a polypropylene container and preserved at 60° C. for 4 weeks, and then the content of 2-amino-3-(4-bromobenzoyl)phenylacetic acid and the pH in each eye drop were measured.

TABLE 2

| Components | | A-04 | A-05 | A-06 | A-07 | A-08 |
|---|---|---|---|---|---|---|
| Sodium 2-amino-3-(4-bromobenzoyl)phenyl-acetate | | 0.1 g | 0.1 g | 0.1 g | 0.1 g | 0.1 g |
| Boric acid | | 1.1 g | 1.1 g | 1.1 g | 1.1 g | 1.1 g |
| Borax | | 1.1 g | 1.1 g | 1.1 g | 1.1 g | 1.1 g |
| Benzalkonium chloride | | 0.005 g | 0.005 g | 0.005 g | 0.005 g | 0.005 g |
| Polysorbate 80 | | — | — | — | — | — |
| Tyloxapol | | 0.02 g | 0.05 g | 0.03 g | — | — |
| Polyoxyl 40 stearate | | — | — | — | 0.02 g | 0.05 g |
| Polyvinyl-pyrrolidone (K-30) | | 2.0 g | 2.0 g | 2.0 g | 2.0 g | 1.0 g |
| Sodium edetate | | 0.02 g | 0.02 g | 0.02 g | 0.02 g | 0.02 g |
| Sodium hydroxide | | q.s. | q.s. | q.s. | q.s. | q.s. |
| Sterile purified water | | q.s. | q.s. | q.s. | q.s. | q.s. |
| Total volume | | 100 mL | 100 mL | 100 mL | 100 mL | 100 mL |
| pH | | 8.17 | 8.16 | 8.15 | 8.19 | 8.19 |
| 60° C., 4 weeks | Remaining rate (%) | 92.6 | 90.9 | 92.0 | 93.4 | 93.1 |
| | pH | 8.15 | 8.16 | 8.15 | 8.13 | 8.14 |

Table 2 shows the remaining rate and the pH of sodium 2-amino-3-(4-bromobenzoyl)phenylacetate after storage at 60° C. for 4 weeks, when the remaining rate of sodium 2-amino-3-(4-bromobenzoyl)phenylacetate at the time of production of eye drops is set to 100%. The remaining rate is a value obtained by correcting moisture vaporization from the container. As is apparent from Table 2, the remaining rate of sodium 2-amino-3-(4-bromobenzoyl)phenylacetate in the compositions A-04, A-05, A-06, A-07 and A-08 containing 0.02 w/v %, 0.03 w/v % and 0.05 w/v % of tyloxapol or 0.02 w/v % and 0.05 w/v % of polyoxyl 40 stearate is not less than 90% after storage at 60° C. for 4 weeks, which indicates that those compositions have sufficient stability for eye drops.

EXPERIMENTAL EXAMPLE 3

Preservative Effect Test of Aqueous Liquid Preparation Containing Sodium 2-amino-3-(4-bromobenzoyl)phenylacetate Preservative effect test of compositions A-04, A-05 and A-07 of Experimental Example 2 was carried out against *Staphylococcus aureus* (hereinafter referred to as *S. aureus*), *Escherichia Coli* (hereinafter referred to as *E. coli*), *Pseudomonas aeruginosa* (hereinafter referred to as *P. aeruginosa*), *Candida albicans* (hereinafter referred to as *C. albicans*) and *Aspergillus niger* (hereinafter referred to as *A. niger*).

The results are shown in Tables 3-1, 3-2 and 3-3.

TABLE 3-1

| A-04 | Inoculum count | Cell count (CFU/mL) | | | | | |
|---|---|---|---|---|---|---|---|
| | | 6 hours after inoculation | 24 hours after inoculation | 7 days after inoculation | 14 days after inoculation | 21 days after inoculation | 28 days after inoculation |
| S. aureus | $2.1 \times 10^6$ | $3.0 \times 10^1$ | 0 | 0 | 0 | 0 | 0 |
| E. coli | $6.5 \times 10^6$ | 0 | 0 | 0 | 0 | 0 | 0 |
| P. aeruginosa | $5.8 \times 10^6$ | 0 | 0 | 0 | 0 | 0 | 0 |
| C. albicans | $3.2 \times 10^5$ | — | — | 0 | 0 | 0 | 0 |
| A. niger | $1.8 \times 10^5$ | — | — | 0 | 0 | 0 | 0 |

TABLE 3-2

| A-05 | Inoculum count | Cell count (CFU/mL) | | | | | |
|---|---|---|---|---|---|---|---|
| | | 6 hours after inoculation | 24 hours after inoculation | 7 days after inoculation | 14 days after inoculation | 21 days after inoculation | 28 days after inoculation |
| S. aureus | $2.1 \times 10^6$ | $1.7 \times 10^5$ | $2.0 \times 10^1$ | 0 | 0 | 0 | 0 |
| E. coli | $6.5 \times 10^6$ | 0 | 0 | 0 | 0 | 0 | 0 |
| P. aeruginosa | $5.8 \times 10^6$ | 0 | 0 | 0 | 0 | 0 | 0 |
| C. albicans | $3.2 \times 10^5$ | — | — | 0 | 0 | 0 | 0 |
| A. niger | $1.8 \times 10^5$ | — | — | 0 | 0 | 0 | 0 |

TABLE 3-3

| A-07 | Inoculum count | Cell count (CFU/mL) | | | | | |
|---|---|---|---|---|---|---|---|
| | | 6 hours after inoculation | 24 hours after inoculation | 7 days after inoculation | 14 days after inoculation | 21 days after inoculation | 28 days after inoculation |
| S. aureus | $2.7 \times 10^6$ | $3.1 \times 10^4$ | 0 | 0 | 0 | 0 | 0 |
| E. coli | $7.4 \times 10^6$ | 0 | 0 | 0 | 0 | 0 | 0 |
| P. aeruginosa | $8.8 \times 10^6$ | 0 | 0 | 0 | 0 | 0 | 0 |
| C. albicans | $4.6 \times 10^5$ | — | — | 0 | 0 | 0 | 0 |
| A. niger | $1.0 \times 10^5$ | — | — | 0 | 0 | 0 | 0 |

As is apparent from Tables 3-1, 3-2 and 3-3, the preservative effect of composition A-04 was found to be compatible with EP-criteria A in European Pharmacopoeia (EP), and those of compositions A-05 and A-07 were found to be compatible with EP-criteria B.

The EP-criteria A and EP-criteria B are given in the following.

EP-Criteria A:

Viable cell counts of bacteria (S. aureus, P. aeruginosa) 6 hours, 24 hours, and 28 days after inoculation decrease to not more than 1/100, not more than 1/1000, and undetectable, respectively.

Viable cell count of fungi (C. albicans, A. niger) 7 hours after inoculation decreases to not more than 1/100, and thereafter, the cell count levels off or decreases.

EP-Criteria B

Viable cell counts of bacteria (S. aureus, P. aeruginosa) 24 hours and 7 days after inoculation decrease to not more than 1/10 and not more than 1/1000, respectively, and thereafter, the cell count levels off or decreases.

Viable cell count of fungi (C. albicans, A. niger) 14 days after inoculation decreases to not more than 1/10, and thereafter, the cell count keeps the same level as that of 14 days after inoculation.

| Example 1: Eye Drop | |
|---|---|
| Sodium 2-amino-3-(4-bromobenzoyl)phenylacetate 3/2 hydrate | 0.1 g |
| Boric acid | 1.1 g |
| Borax | 1.1 g |
| Benzalkonium chloride | 0.005 g |
| Tyloxapol | 0.02 g |
| Polyvinylpyrrolidone (K-30) | 2.0 g |
| Sodium edetate | 0.02 g |
| Sodium hydroxide | q.s. |
| Sterile purified water | to make total volume of 100 mL pH 8.17 |

An eye drop is prepared using the above components in a conventional manner.

| Example 2: Eye Drop | |
|---|---|
| Sodium 2-amino-3-(4-bromobenzoyl)phenylacetate 3/2 hydrate | 0.1 g |
| Boric acid | 1.1 g |
| Borax | 1.1 g |
| Benzalkonium chloride | 0.005 g |
| Tyloxapol | 0.05 g |

-continued

| Example 2: Eye Drop | |
|---|---|
| Polyvinylpyrrolidone (K-30) | 2.0 g |
| Sodium edetate | 0.02 g |
| Sodium hydroxide | q.s. |
| Sterile purified water | to make total volume of 100 mL pH 8.16 |

An eye drop is prepared using the above components in a conventional manner.

| Example 3: Eye Drop | |
|---|---|
| Sodium 2-amino-3-(4-bromobenzoyl)phenylacetate 3/2 hydrate | 0.1 g |
| Boric acid | 1.1 g |
| Borax | 1.1 g |
| Benzalkonium chloride | 0.005 g |
| Polyoxyl 40 stearate | 0.02 g |
| Polyvinylpyrrolidone (K-30) | 2.0 g |
| Sodium edetate | 0.02 g |
| Sodium hydroxide | q.s. |
| Sterile purified water | to make total volume of 100 mL pH 8.19 |

An eye drop is prepared using the above components in a conventional manner.

INDUSTRIAL APPLICABILITY

The aqueous liquid preparation of the present invention in the form of eye drops is useful for the treatment of blepharitis, conjunctivitis, scleritis, and postoperative inflammation. Such preparation is also useful for the treatment of nasal drop for treatment of, for example, allergic rhinitis and inflammatory rhinitis (e.g. chronic rhinitis, hypertrophic rhinitis, nasal polyp, etc.)

The present application is based on application No. 12427/2003 filed in Japan, and includes the entire contents thereof. By reference, the references including patents and patent applications cited herein are incorporated in the present application at the same level as when the entire contents thereof are disclosed. Furthermore, since it is obvious that the present invention can be carried out beyond the description of the above explanation and Working Examples, in light of the foregoing description, various other modifications and changes can be made to the present invention, and thus these modifications and changes should be considered to be within the scope of the claims appended hereto.

The invention claimed is:

1. An aqueous liquid preparation comprising 2-amino-3-(4-bromobenzoyl)phenylacetic acid or a sodium salt or a hydrate thereof, and polyoxyl 40 stearate,
wherein
the concentration of the polyoxyl 40 stearate is selected from a range of a minimum concentration of 0.02 w/v % to a maximum concentration of 0.1 w/v %.

2. The aqueous liquid preparation according to claim 1, wherein the concentration of the 2-amino-3-(4-bromobenzoyl)phenylacetic acid sodium salt or the hydrate thereof is 0.01 to 0.5 w/v %.

3. The aqueous liquid preparation according to claim 1, wherein benzalkonium chloride is contained as a preservative.

4. The aqueous liquid preparation according to claim 1, wherein the pH of the aqueous liquid preparation is within a range of 7 to 9.

5. The aqueous liquid preparation according to claim 4, wherein the pH of the aqueous liquid preparation is within a range of 7.5 to 8.5.

6. The aqueous liquid preparation according to claim 1, wherein the aqueous liquid preparation is an eye drop.

7. The aqueous liquid preparation according to claim 1, wherein the aqueous liquid preparation is a nasal drop.

8. An eye drop comprising sodium 2-amino-3-(4-bromobenzoyl)phenylacetate hydrate and 0.02 to 0.1 w/v % of polyoxyl 40 stearate.

9. A method for stabilizing 2-amino-3-(4-bromobenzoyl)phenylacetic acid sodium salt or a hydrate thereof in an aqueous liquid preparation, which comprises incorporating polyoxyl 40 stearate into an aqueous liquid preparation containing 2-amino-3-(4-bromobenzoyl)phenylacetic acid sodium salt or a hydrate thereof.

10. A method for inhibiting decrease in preservative effect of a preservative in an aqueous liquid preparation of 2-amino-3-(4-bromobenzoyl)phenylacetic acid sodium salt or a hydrate thereof, which comprises incorporating polyoxyl 40 stearate into an aqueous liquid preparation containing 2-amino-3-(4-bromobenzoyl)phenylacetic acid sodium salt or a hydrate thereof and a preservative.

11. The aqueous liquid preparation according to claim 1, which consists essentially of the following two components, wherein the first component is the 2-amino-3-(4-bromobenzoyl)phenylacetic acid sodium salt or the hydrate thereof, and the second component is polyoxyl 40 stearate.

12. The aqueous liquid preparation according to claim 1, which is formulated for ophthalmic administration.

13. The aqueous liquid preparation according to claim 1, wherein when a quaternary ammonium compound is included in said liquid preparation, the quaternary ammonium compound is benzalkonium chloride.

14. The aqueous liquid preparation according to claim 1, which further includes one or more additives selected from the group consisting of a preservative, buffer, thickener, stabilizer, chelating agent, and pH controlling agent.

15. The aqueous liquid preparation according to claim 14, wherein said preservative is benzalkonium chloride; wherein said buffer is boric acid and/or sodium borate; wherein said thickener is polyvinylpyrrolidone; wherein said stabilizer is sodium sulfite; wherein said chelating agent is sodium edetate; and wherein said pH controlling agent is sodium hydroxide.

16. The aqueous liquid preparation according to claim 1, wherein the concentration of the 2-amino-3-(4-bromobenzoyl)phenylacetic acid sodium salt is about 0.2 w/v %.

17. The aqueous liquid preparation according to claim 1, wherein the hydrate is at least one selected from a 1/2 hydrate, 1 hydrate and 3/2 hydrate.

* * * * *